(12) United States Patent
Narayan et al.

(10) Patent No.: US 11,723,591 B2
(45) Date of Patent: *Aug. 15, 2023

(54) METHOD AND APPARATUS FOR ENHANCING NERVOUS FUNCTION

(71) Applicant: Resonea, Inc., Scottsdale, AZ (US)

(72) Inventors: Sanjiv M. Narayan, Palo Alto, CA (US); Ruchir Sehra, Scottsdale, AZ (US)

(73) Assignee: Resonea, Inc., Scottsdale, AZ (US)

(*) Notice: Subject to any disclaimer, the term of this patent is extended or adjusted under 35 U.S.C. 154(b) by 247 days.

This patent is subject to a terminal disclaimer.

(21) Appl. No.: 17/104,316

(22) Filed: Nov. 25, 2020

(65) Prior Publication Data

US 2021/0077014 A1 Mar. 18, 2021

Related U.S. Application Data

(63) Continuation of application No. 16/131,651, filed on Sep. 14, 2018, now Pat. No. 10,849,552, which is a
(Continued)

(51) Int. Cl.
*A61B 5/00* (2006.01)
*A61F 2/72* (2006.01)
(Continued)

(52) U.S. Cl.
CPC ............. *A61B 5/4836* (2013.01); *A61B 5/01* (2013.01); *A61B 5/024* (2013.01); *A61B 5/0205* (2013.01);
(Continued)

(58) Field of Classification Search
CPC ....... A61B 5/4836; A61B 5/296; A61B 5/369; A61B 5/318; A61B 5/389; A61B 5/24;
(Continued)

(56) References Cited

U.S. PATENT DOCUMENTS 6,871,094 B1 3/2005 Mien et al.
8,657,756 B2 2/2014 Stahmann et al.
(Continued)

FOREIGN PATENT DOCUMENTS

CN 1349421 A 5/2002
CN 2590534 Y 12/2003
(Continued)

OTHER PUBLICATIONS

DiGiovanna, et al., "Coadaptive Brain-Machine Interface via Reinforcement Learning", IEEE Transactions on Biomedical Engineering, vol. 56, No. 1, Jan. 2009, 54-64.
(Continued)

*Primary Examiner* — Aaron F Roane
(74) *Attorney, Agent, or Firm* — Hoffmann & Baron, LLP

(57) ABSTRACT

A system and method of treating a sleep disorder, including: detecting signals associated with at least one symptom or sign of the sleep disorder at one or more sensors; processing the signals to create a symbolic representation of the sleep disorder, wherein the symbolic representation indicates a relationship of the signals to the sleep disorder empirically and not based on physiologic mapping of the signals to the sleep disorder; and stimulating a region of a human body to alter the symbolic representation between detected signals and the sleep disorder, wherein the symbolic representation as altered indicates treatment of the sleep disorder.

26 Claims, 11 Drawing Sheets

Related U.S. Application Data continuation of application No. 15/443,888, filed on Feb. 27, 2017, now Pat. No. 10,092,235, which is a continuation-in-part of application No. PCT/US2015/047820, filed on Aug. 31, 2015, which is a continuation-in-part of application No. PCT/US2015/046819, filed on Aug. 25, 2015, said application No. 15/443,888 is a continuation of application No. PCT/US2015/046819, filed on Aug. 25, 2015.

(60) Provisional application No. 62/043,760, filed on Aug. 29, 2014.

(51) Int. Cl.

| | | |
|---|---|---|
| *A61B 5/24* | (2021.01) | |
| *A61B 5/25* | (2021.01) | |
| *A61B 5/296* | (2021.01) | |
| *A61B 5/318* | (2021.01) | |
| *A61B 5/369* | (2021.01) | |
| *A61B 5/389* | (2021.01) | |
| *A61B 5/01* | (2006.01) | |
| *A61B 5/0205* | (2006.01) | |
| *A61B 5/024* | (2006.01) | |
| *A61B 5/0531* | (2021.01) | |
| *A61B 5/08* | (2006.01) | |
| *A61B 5/145* | (2006.01) | |

(52) U.S. Cl.
CPC .......... *A61B 5/0531* (2013.01); *A61B 5/0816* (2013.01); *A61B 5/14539* (2013.01); *A61B 5/24* (2021.01); *A61B 5/25* (2021.01); *A61B 5/296* (2021.01); *A61B 5/318* (2021.01); *A61B 5/369* (2021.01); *A61B 5/389* (2021.01); *A61B 5/40* (2013.01); *A61B 5/6877* (2013.01); *A61B 5/7267* (2013.01); *A61F 2/72* (2013.01); *A61B 2560/0242* (2013.01)

(58) Field of Classification Search
CPC .......... A61B 5/25; A61B 5/01; A61B 5/0205; A61B 5/024; A61B 5/0531; A61B 5/0816; A61B 5/14539; A61B 5/40; A61B 5/6877; A61B 5/7267; A61B 2560/0242; A61F 2/72
USPC ......................................................... 600/301
See application file for complete search history.

(56) References Cited

U.S. PATENT DOCUMENTS

| | | |
|---|---|---|
| 2008/0300572 A1 | 12/2008 | Rankers et al. |
| 2011/0137197 A1 | 6/2011 | Stahmann et al. |
| 2011/0218453 A1 | 9/2011 | Hirata et al. |
| 2013/0030257 A1 | 1/2013 | Nakata |
| 2013/0325082 A1 | 12/2013 | Schuler |
| 2015/0018706 A1 | 1/2015 | Segal |

FOREIGN PATENT DOCUMENTS

| | | |
|---|---|---|
| CN | 201453834 U | 5/2010 |
| CN | 203204285 U | 9/2013 |
| CN | 103917156 A | 7/2014 |
| EP | 0 421 780 A2 | 4/1991 |
| EP | 0467695 A2 | 7/1991 |
| EP | 1 043 003 A1 | 10/2000 |
| JP | 04-250169 A | 7/1992 |
| JP | 05-111881 A | 5/1993 |
| JP | 2004-529707 A | 9/2004 |
| JP | 2011-186667 A | 9/2011 |
| JP | 2014-514043 A | 6/2014 |
| WO | WO 02/087433 A1 | 11/2002 |
| WO | 2012/129574 A2 | 9/2012 |

OTHER PUBLICATIONS

Nicolelis, Miguel A.L., et al., "Controlling Robots with the Mind", Scientific American, Oct. 2002, pp. 46-53.

Written Opinion for International Application No. PCT/US2015/046819, dated Dec. 1, 2016.

International Search Report for International Application No. PCT/US2015/046819, dated Dec. 1, 2016.

Mialasri et al., "Securing Wireless Implantable Devices for Healthcare: Ideas and Challenges", IEEE Communications Magazine, vol. 47, No. 7, Jul. 1, 2009, pp. 74-80.

Alemdar et al., "Wireless Sensor Networks for Healthcare: A Survey", Computer Networks, vol. 54, No. 15, Oct. 28, 2010, pp. 2688-2710.

Ko, et al., "Wireless Sensor Networks for Healthcare", Proceedings of the IEEE, vol. 98, No. 11, Nov. 1, 2010, pp. 1947-1960.

Paul et al., "A Review of the Security of Insulin Pump Infusion Systems", Journal of Diabetes Science and Technology, vol. 55, No. 6, Nov. 1, 2011, pp. 1557-1562.

International Search Report for International Application No. PCT/US2015/047820, dated Dec. 1, 2016.

Written Opinion for International Application No. PCT/US2015/047820, dated Dec. 1, 2016.

METHOD AND APPARATUS FOR ENHANCING NERVOUS FUNCTION

CROSS-REFERENCE TO RELATED APPLICATIONS

This application is a continuation of U.S. Ser. No. 16/131,651, filed Sep. 14, 2018, which in turn is a continuation of U.S. Ser. No. 15/443,888, filed Feb. 27, 2017, now U.S. Pat. No. 10,092,235, issued Oct. 9, 2018, which in turn is a continuation of International Application No. PCT/US2015/046819, filed Aug. 25, 2015, which in turn claims priority to U.S. Provisional Application No. 62/043,760, filed Aug. 29, 2014, the entire contents of which are incorporated by reference in their entirety; U.S. Ser. No. 15/443,888, filed Feb. 27, 2017, now U.S. Pat. No. 10,092,235, issued Oct. 9, 2018, is also a continuation-in-part of International Application No. PCT/US2015/047820, filed Aug. 31, 2015, which in turn claims priority to U.S. Provisional Application No. 62/043,760, filed Aug. 29, 2014; International Application No. PCT/US2015/047820 is also a continuation-in-part of International Application No. PCT/US2015/046819, filed Aug. 25, 2015, which in turn claims priority to U.S. Provisional Application No. 62/043,760, filed Aug. 29, 2014, the entire contents of which are incorporated by reference in their entirety. The entire contents of each of these priority documents (U.S. Ser. Nos. 16/131,651, 15/443,888, and 62/043,760, and International Application Nos. PCT/US2015/046819 and PCT/US2015/047820) are incorporated herein by reference in their entirety.

BACKGROUND

Field

The present application relates generally to function of the nervous system of the body. More specifically, the present application is directed to a method, system and apparatus to modify or enhance nervous control of the body for use in normal individuals or patients with disease.

Brief Discussion of Related Art

Several functions of the body are mediated by the brain (central nervous system) and/or peripheral nervous system. These functions include classical "neurological" functions such as vision or hearing, but also nearly all activities of daily life, including learning, moving, or operating machinery.

In many situations, the body's ability to perform such functions is constrained. Constraint can take many forms and may be physical or functional. Physical constraints include an external obstacle preventing movement of a limb in an enclosed space such as may affect a warrior or scuba diver. A physical constraint may also be internal, such as loss of a limb from amputation. Functional constraints may include a classical disease, such as stroke that prevents an individual's ability to move the foot. However, functional constraints may also include underperformance on a task due to insufficient training, knowledge or acquisition of skills, or through disuse.

Many attempts have been made to address some of these constraints, using a familiar paradigm that body sensors (e.g., the eye), nervous function (e.g., the central and peripheral nervous system) and effector organs (e.g., a muscle group) can be often be functionally mapped to specific anatomic locations.

Conscious and purposeful interventions are hence applied when these functions are constrained, e.g., a soldier can use a finger to activate a device if his/her foot cannot activate a pedal due to an obstacle or, in an amputee, interfacing a robotic arm to specific nerve fibers that formerly controlled the biological arm.

However, the functional mapping required for classical solutions to address constraints is complex. Such functional mapping or 'atlases' are debated even for some "simple sensations" such as visual recognition of a face, and far less clear for complex functions such as alertness. Much data has come from animal models that are not well suited to model or analyze the neuroanatomical basis of thought or complex human activity.

Numerous body functions show considerable variation between individuals and are imprecisely defined by mapping including as mood, alertness, learning how to operate machinery, forms of exercise, or other complex sensory-motor activities. Some of these functions are essential for normal activity, and others for high-demand activities such as in combat or during competitive athletics.

Currently, machines that interface with, augment or aid human function are largely predicated on a detailed knowledge of neuroimaging, cortical mapping and even peripheral nerve mapping of documented normal and abnormal functions/pathways. Such machines have largely attempted to replace, improve or reinstate function based upon the normal documented functions and pathways.

In the case of full virtual function, the goal is usually to create an illusionary or representative environment by feeding specific sensory inputs (primarily visual, tactile and/or auditory) to, again, replicate the normal documented pathways and real-world existing experiences. Unfortunately, such approaches have often limited the benefits of the technologies due to the fact that normal pathways vary from individual to individual. Thus, simulating normal often may not accurately replicate that function for an individual nor represent normal for that individual.

Conversely, it would be of immense benefit to society to construct a device able to restore/enhance such human functionality, i.e., to compensate for the constraints alluded to above, without the need to define or replicate precise neural pathways for device interfacing, or without the need to consciously alter the function (e.g., training to use a finger instead of a foot to operate a pedal). Currently, there are few methods in the prior art to achieve this goal. Such devices could be used to enhance performance in individuals without disease, or restore lost function in those with disease.

SUMMARY OF THE PRESENT INVENTION

The invention is able to enhance performance of function or re-instate (treat/replace) a lost function, even a complex function, using sensors to detect signals naturally associated with that function, engineering circuits based on mathematical formation of a new symbolic code representing that function, and an effector that can enhance or reinstate said function. No a priori logic or programming is required to use the invention. The invention uses the brain to figure out its own logic and "piggy-back" on the brains ability to recognize patterns, in other words, uniquely interfaces with existing brain functionality in order to produce a desired result, e.g., re-task, enhance or otherwise produce a desired function.

Because the nervous system also interacts with other systems in the body, including the immune system and endocrine system, this invention can be used to guide or interact with other organ systems including destroying cancer cells, altering lung function or altering a function of the gastrointestinal or genitourinary tracts.

Accordingly, this invention is an enciphered nervous system (ENS), linking sensors (natural biological or artificial devices) to specific tasks (existing biological nerves/muscles or via engineered devices) using a programmable ENS. This ENS can be programmed to restore/augment a function, to form a new program using existing biological elements ('retasking' a function to circumvent physical limitation) or to form a new program using hybrid artificial and biological elements to enhance a function—such as hearing outside the normal frequency range or sensing a stimulus for which there is no physiological sensor (e.g., some toxins).

The functional symbolic code generated by this invention is specific to a task. It is primarily specific to an individual ("personalized enciphered nervous system"), since mapping of any task differs between individuals—that has greatly limited the success of, for example, neurophysiological prostheses to date. For certain tasks, it can use inputs from other individuals using an associative population-based approach ("crowd-sourced enciphered nervous system"). This is required for some applications in which personal exposure/training must be avoided (e.g., using nomograms of population-derived dangerous levels of certain toxins). The mathematical approaches employed in the crowd-sourced approach are empirical and functional, thus circumventing some of the limitations of detailed neurophysiological and neuropathological atlases due to the natural biological variation between individuals that create differences from the "normal" pathways Limitations are circumvented using artificial neural networks for "learning" the functional association, and using hybrid approaches including associated signals from that individual.

Thus, the current invention forms a symbolic internal representation of simple and complex functions. This internal representation is derived from empiric association between detected signals and a function—e.g., electrical signals on the hand when a finger touches an object, or scalp signals when an individual is "alert" versus drowsy. This is actionable, yet more simple and a more tractable computational task. It is akin to representing something that is visualized by an "impressionist" painter rather than one trained in the "realist" school. This approach is based largely on the premise that in addition to the primary brain cortex required for a task, that is difficult to precisely define, secondary areas become activated and may be easily sensed and used for training.

The current invention is based on the known observation that under certain conditions of disease or training, cortical plasticity is well described (e.g., DARPA limb projects, stroke victims recovering function years later). Plasticity is also observed in peripheral nerves, such that the dermatomal distribution of a functioning peripheral nerve can expand when an adjacent distribution is served by a diseased nerve. In other words, the same function can now be served by different regions of the central or peripheral nervous system. For the purposes to the invention, the term "plasticity" means the ability of neurons to adapt and change in response to a stimulus from the environment. For example, the neural pathways and synapses may change in response to changes in environment, behavior, emotions (moods), new stimuli, thinking, neural processing injury and combinations thereof. For example, a hat which cools the head, allows the hat to be worn and include such hardware as sensing and stimulating components which can interact with various and specific regions of the head to achieve the desired result.

At a fundamental level, this 'plasticity' does not require knowledge of the precise underlying neurophysiological mapping. For instance, in classical Pavlovian training, rats were taught to salivate from non-food-related stimuli that were previously associated with food during training. In other words, a new stimulus—biological function can be programmed. The current invention uses sophisticated sensors, mathematical approaches, and effector devices to do this in a deterministic fashion tailored to a desired task.

The current invention does not focus on, nor rely upon, a priori knowledge of known functions/pathways, that are often complex and possibly undefined, but rather focuses on customized, individualized solutions best suited to perform specific functions through, potentially unused, capacity in pathways.

The current invention is further based on the concept that the body can be considered a multipurpose computer, comprising sensors, processing elements, and effector pathways/organs. It should be possible to design a symbolic code to access or "reprogram" this function to map specific sensors to specific effectors throughout the body.

The current invention is further based on the concept that the body has certain neural processing capacity, of which only a minority is used even in highly stressful human activities such as warrior combat (e.g., 40% capacity used). In highly focused, non-life-or-death situations, a minority is still used, likely 20-40%, e.g., NBA finals, SAT testing. Therefore there is substantial residual capacity at any one time.

Tapping this capacity could improve performance, substitute for a lost capability (e.g., amputee, stroke victim), replace an external computer with an intrinsic biological computing function, or retask processing representation of an existing function (e.g., golf swing, noxious effect such as mild pain for incorrect task/function).

Tapping this capacity/functionality could also be used to recruit and reprogram certain (unused) portions of the body like a multipurpose computer to perform a task e.g., controlling a remote control unit, or bioencoding of information in the parietal lobe to exploit the human brain's unparalleled ability for pattern recognition.

This may be done in many ways. One is to use an existing and/or unused body capacity by stimulating defined neuronal patterns. This will vary based on frequencies, amplitudes and sites of stimulation, some of which may be based on population (crowd-sourced) data. To avoid inadvertent recruitment of an existing bodily function, the invention can stimulate the unused capacity in a non-physiological or atypical physiological pattern. This would involve the use of neural frequencies/patterns that are not part of normal processing or pathways. This may avoid invoking behavioral change, sensation by the brain and/or changing memory of an event (Redondo et al., Nature 2014).

Numerous types of sensors can be used. Examples include solid physical sensors such as FINE (singularityhub.com/2013/07/24/darpas-brain-controlled-prosthetic-arm-and-a-bionic-hand-that-can-touch/), traditional ECG- or EEG-electrical sensors, non-solid sensors such as electrostatic creams, piezoelectric film sensors, printed circuit sensors, photosensitive film, thermosensitive film, and external-oriented sensors not in contact with the body such as video, IR, temperature, gas sensors, etc. These external-oriented sensors detect the external world's stimuli and transduce the information through a constructed/created (non-standard or non-somatotopic) path to active nerves.

Processing elements could include a digital signal processor which interfaces with output elements that can stimulate different parts/nerves of the body, or cause mechanical action in an external machine. Such elements could include traditional computing machines with integrated circuits in isolation or networked (e.g., cloud computing), biological computing, or utilizing unused capacity in the human brain to perform specific, directed computing tasks.

Effector elements could include direct electrical outputs or mechanical machines such as nerve stimulating electrodes or servo motors to control a limb, digitized electronic signals such as radiofrequency or infrared transmissions, or even virtualized data such as avatars in a virtual world interface or elements in a large database that can be queried.

Applications of these effector elements can be for diagnostic purposes such as understanding different stimuli or body functions (e.g., visual function, visual disease progression, mood, alertness, detecting injury such as traumatic brain injury, cardiac electrical and/or mechanical function, subclinical seizure detection), learning about external world situations or environments without subjecting the human body to discomfort (e.g., sensing heat in a fire, detecting oxygen or toxic gas content in the external environment such as a mine).

Effector devices or elements can be applied for medically related therapy such as for brain related function (e.g., mood disorders treated with brain stimulation, treating alertness in patients with sleep disorders or central apnea, biofeedback for stroke rehabilitation, deep brain stimulation for motion or seizure disorders), other neurological diseases (e.g., notifying patients with peripheral neuropathy of dangerous or noxious stimuli), cardiac disease (e.g., arrhythmias treated with implanted devices, cardiac function improved with mechanical or electrical devices), or other organ disease modified with directed electrical or mechanical elements.

Applications of these effector elements can be for training, learning and performing of unusual physiological activities or mechanical, non-physiologic functions. Examples of unusual physiologic applications include enhancing learning or military and civilian applications via transcranial direct current stimulation (ref: www.scientificamerican.com/article/amping-up-brain-function), improving athletic performance (e.g., noxious biofeedback for incorrect motions/activities, pleasing brain stimulation for correct motions/activities, enhancing sensory perceptions (e.g., augmented visual sensors feeding facial recognition information via lesser used pathways such as body propriosensors for use by security forces, auditory sensors stimulating auditory pathways in response to subthreshold or previously inaudible information), performing typical tasks in non-typical ways either by overcoming constraints or developing more efficient solutions (e.g., driving a car with small finger movements or eye motion, analyzing big data with motor movements such as scanning and arranging data with virtual fingers and hands). Examples of mechanical functions include operating a mechanical exoskeleton for soldiers, performing tasks that are too difficult or dangerous for humans such as deep sea exploration, armed combat, or even as basic as controlling video games or remote controls.

Specific central or peripheral neural functions are controlled by specific patterns of neuronal firing. A device can mimic these patterns to effect the prior function—for instance, stimulating a nerve using physiological patterns to control a disused muscle. This functionality can also be applied without direct knowledge or access to the primary muscle. Many functions produce nerve activity at the body surface that may be co-localized, e.g., dermatomal distributions of mixed peripheral nerves. One example is sensation of the tip of shoulder blade at the "C234" region, control of deltoid muscle function by the "C56" region, and control of the diaphragm muscles and hence breathing at the "C345" region. This can be performed empirically, without the direct need for detailed neuroimaging studies.

In one aspect, there is provided a method for interacting with the nervous system, the method including detecting signals associated with a biological function at one or more sensors, processing said signals to create a representation, delivering effector responses based on the symbolic representation, and controlling a physical process.

In another aspect, there is provided a method to enhance performance of a task, the method including detecting signals associated with the task at one or more sensors, creating a representation of said task, delivering effector responses to modify said representation, and enhancing performance of said task.

In another aspect, there is provided a method to treat a disease, the method including detecting signals associated with said disease at one or more sensors, creating a core symbolic representation of said disease, stimulating a region of the body to alter the representation between detected signals and the disease, and treating the disease.

In another aspect, there is provided a method for transforming sensed nerve activity, the method including detecting signals associated with a biological function at one or more sensors, processing said signals to create a representation, delivering effector responses based on the representation, and controlling a biological function.

In another aspect, there is provided a method for controlling a device using biological signals, the method including detecting biological signals from the body using one or more sensors, converting detected biological signals from the sensor to electronic representation, and outputting electronic information in a recognizable format to electromechanically control a device.

In another aspect, there is provided a method to measure visual function, the method including detecting biological signals of biological sensory activation, processing these signals to provide quantitative measures of sensation, creating a representation of said sensory activation, and, optionally, using the representation to determine optimal treatment.

In another aspect, there is provided a method for improving specific human performance, the method including identifying regions of the body associated with parts of the brain that serve a specific function, placing low energy stimulating electrodes proximate to said regions of the body, applying stimulation through said electrodes to activate said parts of the brain, and measuring changes in performance related to said parts of the brain.

In another aspect, there is provided a system for interacting with the nervous system, the system including a processor, a memory storing instructions that, when executed by the processor, performs operations including detecting signals associated with a biological function at one or more sensors, processing said signals to create a representation, delivering effector responses based on the symbolic representation, and controlling a physical process.

In another aspect, there is provided a system to enhance performance of a task, the system including a processor, a memory storing instructions that, when executed by the processor, performs operations including detecting signals associated with the task at one or more sensors, creating a representation of said task, delivering effector responses to modify said representation, and enhancing performance of said task.

In another aspect, there is provided a system to treat a disease, the system including a processor, a memory storing instructions that, when executed by the processor, performs operations includes detecting signals associated with said disease at one or more sensors, creating a core symbolic representation of said disease, stimulating a region of the body to alter the representation between detected signals and the disease, and treating the disease.

In another aspect, there is provided a system for transforming sensed nerve activity, the system including a processor, a memory storing instructions that, when executed by the processor, performs operations including detecting signals associated with a biological function at one or more sensors, processing said signals to create a representation, delivering effector responses based on the representation, and controlling a biological function.

In another aspect, there is provided a system for controlling a device using biological signals, the system including a processor, a memory storing instructions that, when executed by the processor, performs operations including detecting biological signals from the body using one or more sensors, converting detected biological signals from the sensor to electronic representation, and outputting electronic information in a recognizable format to electromechanically control a device.

In another aspect, there is provided a system to measure visual function, the system including a processor, a memory storing instructions that, when executed by the processor, performs operations including detecting biological signals of biological sensory activation, processing these signals to provide quantitative measures of sensation, creating a representation of said sensory activation, and optionally, using the representation to determine optimal treatment.

In another aspect, there is provided a system for improving specific human performance, the system including a processor, a memory storing instructions that, when executed by the processor, performs operations including identifying regions of the body associated with parts of the brain that serve a specific function, placing low energy stimulating electrodes proximate to said regions of the body, applying stimulation through said electrodes to activate said parts of the brain, and measuring changes in performance related to said parts of the brain.

BRIEF DESCRIPTION OF THE DRAWINGS

Some embodiments are illustrated by way of example and not limitation in the figures of the accompanying drawings, in which.

DETAILED DESCRIPTION

Systems, methods, and devices for enhancing and modifying functions of the nervous system are disclosed herein. In the following description, for the purposes of explanation, numerous specific details are set forth in order to provide a thorough understanding of example embodiments. It will be evident, however, to one skilled in the art, that an example embodiment may be practiced without all of the disclosed specific details. It is also evident that various components, elements, and/or steps of difference embodiments may be combined.

Figure 1:
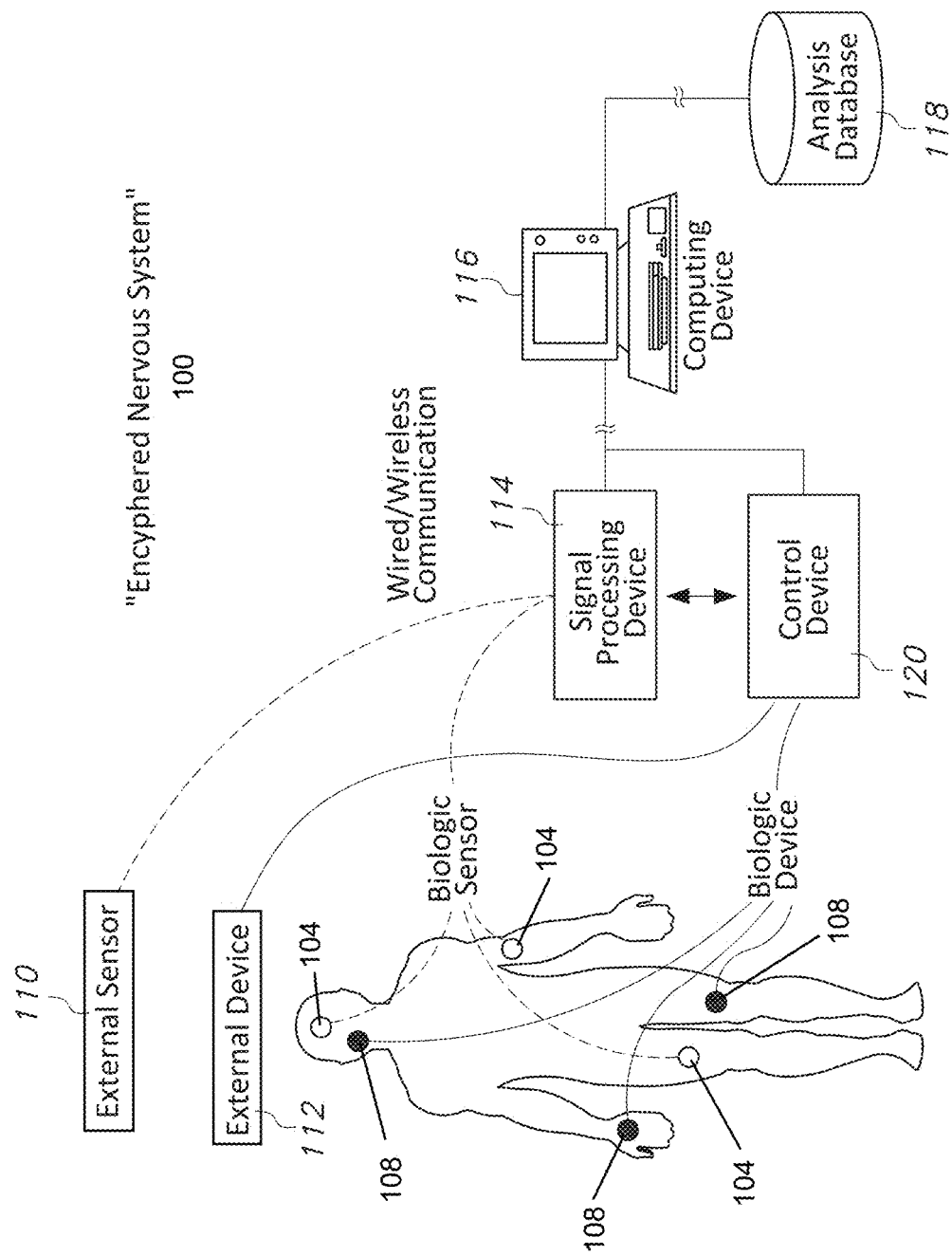
FIG. 1 is a schematic representation of the invention, including sensors for biological and non-biological signals, a processing unit that produces a symbolic representation of specific nervous functions, or an "enciphered nervous system", and a control unit to alter nervous function or control a device.

FIG. 1 illustrates an example system to modify and enhance functionality of the nervous system in a human being. Specifically, the example system 100 is configured to access external signals from biological sensors 104 and from external sensors 110.

Biological sensors 104 include, but are not limited to, sensors for transcutaneous or invasive nerve activity (neural electrical activity), muscle electrical activity (myopotentials), of mechanical activity (mechanoreceptors), skin resistance (a measure of body chemistry), body temperature (a measure of metabolic activity and other disease states), body pH (from the skin, mouth, or other regions of the gastrointestinal or genitourinary tracts), enzymatic profile (for instance, from a probe in the gastrointestinal tract), DNA profile (for instance, a gene chip on the lining of the mouth), heart rate, ventilating (breathing) rate, or any other body signal.

External sensors 110 can sense biological signals, from that individual, from another individual or from a database of signals 118.

External sensors 110 can provide many types of information including, but not limited to, those normally sensed including pressure/physical movement (tactile, touch sensation), temperature (thermal sensation), sound (auditory sensation), electromagnetic radiation in the visible spectrum (visual sensation), movement (a measure of muscle function and balance).

External sensors 110 can provide information related to normal sensation but that is not normally sensed including, but not limited to, the invisible electromagnetic spectrum (such as gamma radiation, X-rays, radiowaves), sound waves outside the normal physiological range for humans (roughly 20 Hz to 20 kHz) but including the range sensed by animals (for instance, dogs can sense higher frequencies).

External sensors 110 can provide information that is not normally sensed including, but not limited to, toxins such as carbon monoxide or excessive carbon dioxide, forms of radiation (such as alpha and beta radiation), biotoxins such as toxins of *Escherichia coli* bacteria associated with food poisoning (type 0157), anthrax or other agents. Clearly, such information would be of value for military and security applications.

In FIG. 1, signals (internal or external) are delivered either wirelessly or via wired communication to a signal processing device 114 functioning in concert with a computing device 116 that has access to an analysis database 118. The computing and signal processing devices 116, 114 communicate with a control device 120, that in turn directly controls a biological device (e.g., a body part of body function) 108 or an external device 112 (e.g., remote control, medical device). The computing, signal processing, and control devices 116, 114, 120 with sensors 104, biological devices 108, and effector devices 115 together form an "enciphered nervous system" (ENS).

Figure 2:
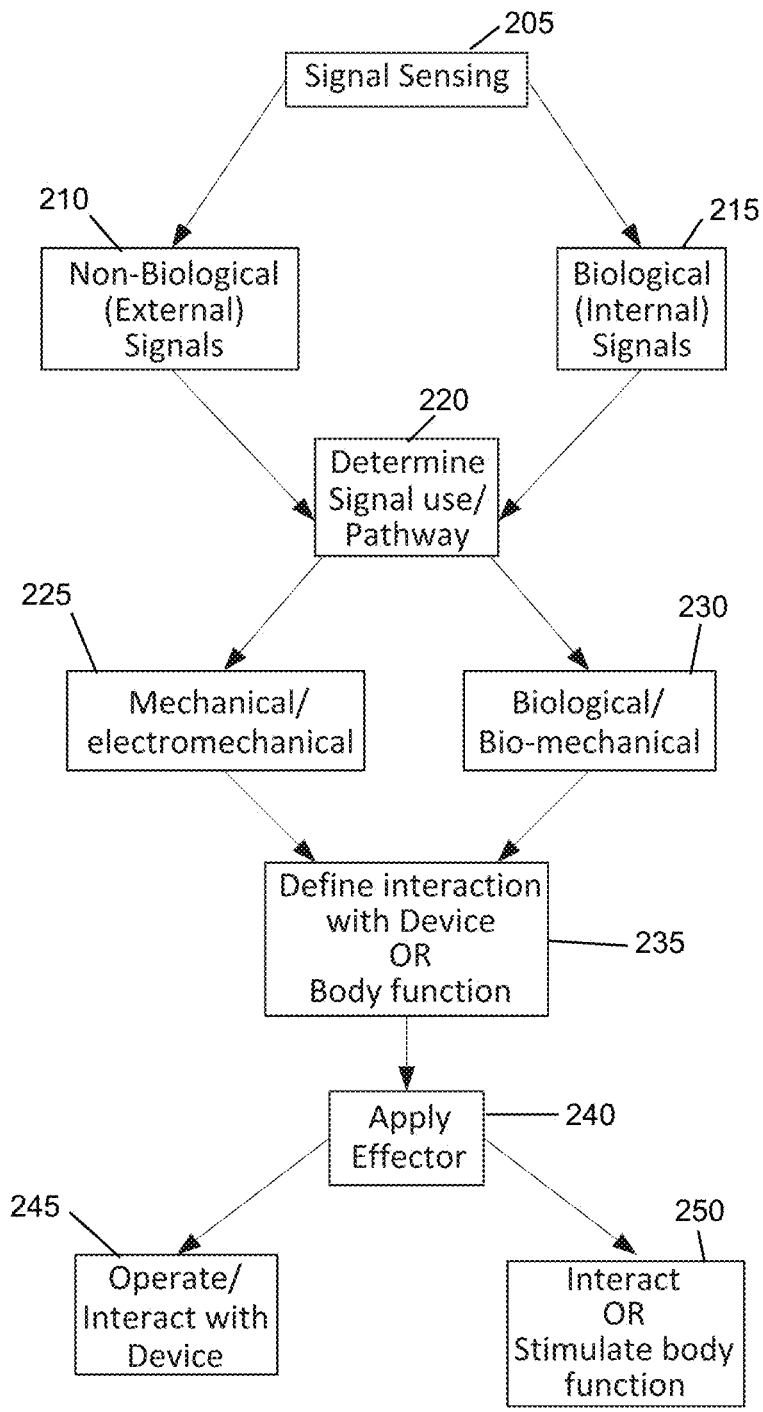
FIG. 2 is a flowchart indicating general functionality of the invention for biological and non-biological sensed signals.

FIG. 2 give more detail on the inventive process of the "enciphered nervous system". Signals are sensed (205) as either non-biological (210) or biological (215), although these signals can be combined and multiplexed.

In FIG. 2, element 220 is the core computational element that functions as the central nervous system of the ENS. This computational element forms a symbolic relationship between the signal and a biological function. This symbolic relationship is mathematical. Notably, this relationship is empirical and functional—it is not based on a detailed neurophysiological mapping of the function. It is also not necessarily based on the primary "classical" neurological loop. For instance, sufficient pain in the leg causes elevated nerve activity in other parts of the body. This can be sensed as "associated with the pain" sensation, from a sensor in a more convenient part of the body. The empirical functional relationship is mathematical, and can be deterministic (e.g., equation based), or can be trained/learned such as via neuronal network.

In the simplest case, the symbolic relationship is a matrix in which a signal X causes a function Y; for instance, a noxious stimulus such as pain sensed by a sensor/sensory nerve in the leg (X) causes activity in a motor nerve causing withdrawal of that leg (Y). This function is not represented in the device based upon a detailed neurophysiological representation of leg sensation (in the primary somatosensory cortex, in the post-central gyms), or the precise nerves that control the leg. Instead, this function is mapped empirically—sensation on any nerve associated with the painful stimulus can result in actions leading to leg withdrawal.

The inventive advantage of this approach is that it exploits the pleiotropic effects of any particular stimulus. For instance, an acute painful stimulus often produces activation on nerves remote from the original site of stimulation. Hence, pain in the leg, that may be inaccessible, may be detected from nerve activity quite distant from the sensation such as the chest wall, that may be more accessible.

In FIG. 2, Step 220 is followed by a mechanical action (225) or biological action (230). For instance, the sensed noxious stimulus can produce an effector function to move the leg (biological, 230), or control a device to administer a pain killing medication or therapy (device, 225). In other examples that will be discussed below, the stimulus can move a prosthetic limb (mechanical, 225) or alter biological function (230).

Figure 11:
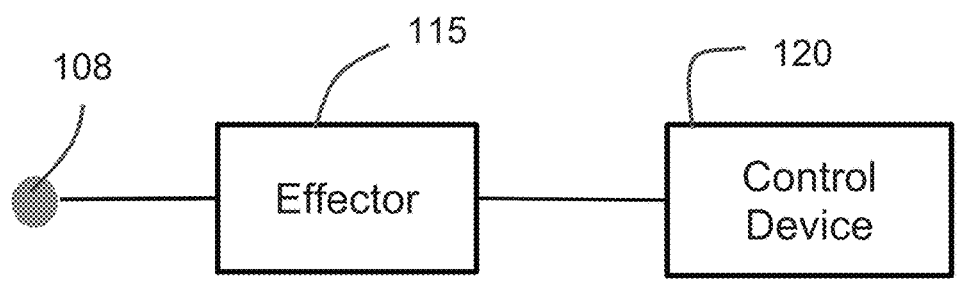
FIG. 11 is a block diagram of an illustrative embodiment of an effector in use with a biological device and a control device.
Figure 12:
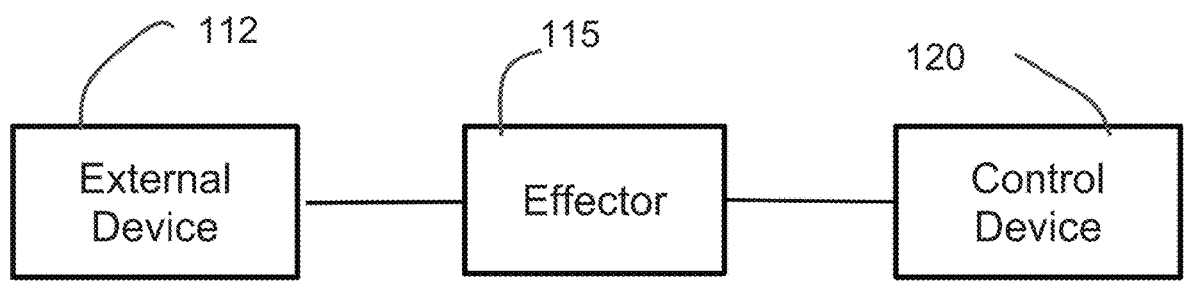
FIG. 12 is a block diagram of an illustrative embodiment of an effector in use with an external device and a control device.

FIG. 2 further indicates that the precise action is determined by the ENS by defining the interaction with the device or bodily function (step 235). This is a programmed function, depending upon the desired functionality of the invention. This then produces a real output, such as effector 115, requiring energy application (step 240) that results in interaction with the device (step 245), as depicted in FIGS. 11 and 12, or a bodily function (step 250).

Thus, FIG. 2 summarizes the invention as a parallel artificial central and peripheral nervous system that pairs sensed function to effector function in programmed ways. In the simplest case, the sensed and effector functions are natural physiological functions, such as sensing a painful stimulus from the leg and moving the leg away. In more complex and practical ways, the invention provides the ability to enhance normal function (performance enhancement), enhance impaired function to treat a disease or in cases where normal function cannot be manifest (e.g., in warfare or other situations of constraint).

The invention as described in FIG. 1 and FIG. 2 may require general information on how certain sensed signals cause damage, to calibrate sensing and delivery of therapy functions. For instance, exposure to carbon monoxide is dangerous, yet this toxin is often undetected. Federal agencies in the U.S. such as OSHA put a highest limit on long-term workplace exposure levels of 50 ppm, with a "ceiling" of 100 ppm. Exposures of 800 ppm (0.08%) lead to dizziness, nausea, and convulsions within 45 min, with the individual becoming insensible within 2 hours. The present invention detects this toxin early and causes biofeedback through the enciphered nervous system, hence having extremely practical implications in industrial environments. Other nomograms to identify thresholds for "safe" versus and "actionable" exposure to various stimuli are contemplated, including but not limited to chemicals, biological toxins, radiation, electrical stimuli, visual stimuli and auditory stimuli. The present invention provides methods and systems to detect and provide feedback mechanisms and to develop such practical applications for therapy or creating safer environments.

The invention as described in FIG. 1 and FIG. 2 can also be used to create totally novel human functionality, by using the engineered artificial "enciphered nervous system" to pair sensed biological or external signals to any programmed biological or external device function. It thus forms an embodiment of a cybernetic nervous system operating in parallel with the body's natural nervous system. The extent to which this these nervous systems are parallel or integrated will depend upon the extent to which sensed signals are multiplexed and effector "control" signals are combined. Examples are discussed below.

The invention as described in FIG. 1 and FIG. 2 thus provides hitherto unavailable programmatic control of plasticity—that is actually observed at some level on a regular basis in normal life. In the realm of sensory physiology, training can enable an individual to perceive a sensation that was previously present but not registered/recognized Examples include musical training to detect tonality, or combat training to detect subtle sounds or visual cues. In the realm of motor control, physical training can enable an individual to use muscle groups that were previously unused. In the realm of disease, normal "healing functions" cause undiseased regions of the central nervous system to take over functions now lost due to a stroke (cortical plasticity), or unaffected peripheral nerves to take over functions of a nerve lost due to trauma or neuropathy (expansion/plasticity of peripheral dermatomes).

The invention also substantially extends normal plasticity—by programming desired and directed regions of the body to sense and effect functions normally reserved for other regions of the body that are currently inaccessible (e.g., in military combat) or unavailable (e.g., due to disease).

The invention also substantially advances normal plasticity by integrating external sensors (e.g., for normally inaudible sound frequencies or sensations) or devices (e.g., prosthetic limbs, other electronic devices) into the ENS.

Thus, this invention can improve and enhance function of traditional senses, if a device is used that integrates sensors that sense outside the normal physiological range can be used to enhance the range of normal physiological sensation. For instance, sensing signals in the "inaudible to humans" part of the frequency spectrum, transducing the signal to the audible range, and transmitting it via bony conduction using a device could be used for private communication, encryption, recreational or other purposes. Medically, this invention could be used to compensate for hearing loss. This same invention with sensors of vibration could be used to compensate for loss of this sensation in certain neurological diseases such as peripheral neuropathy, by transmitting this sensation to an intact sensation in a different part of the body.

Important safety issues must be raised at this stage. While no untoward, dangerous or otherwise undesired functionality has been observed with this invention, certain limits must be imposed. First, stimulation intensity provided by the device can be controlled such that painful or dangerous levels are not reached. Second, sensory input can be controlled such that disturbing or undesired levels are not reached. Third, any sensor or device (effector) used desirably may have acceptable and tested safety profiles.

Figure 3:
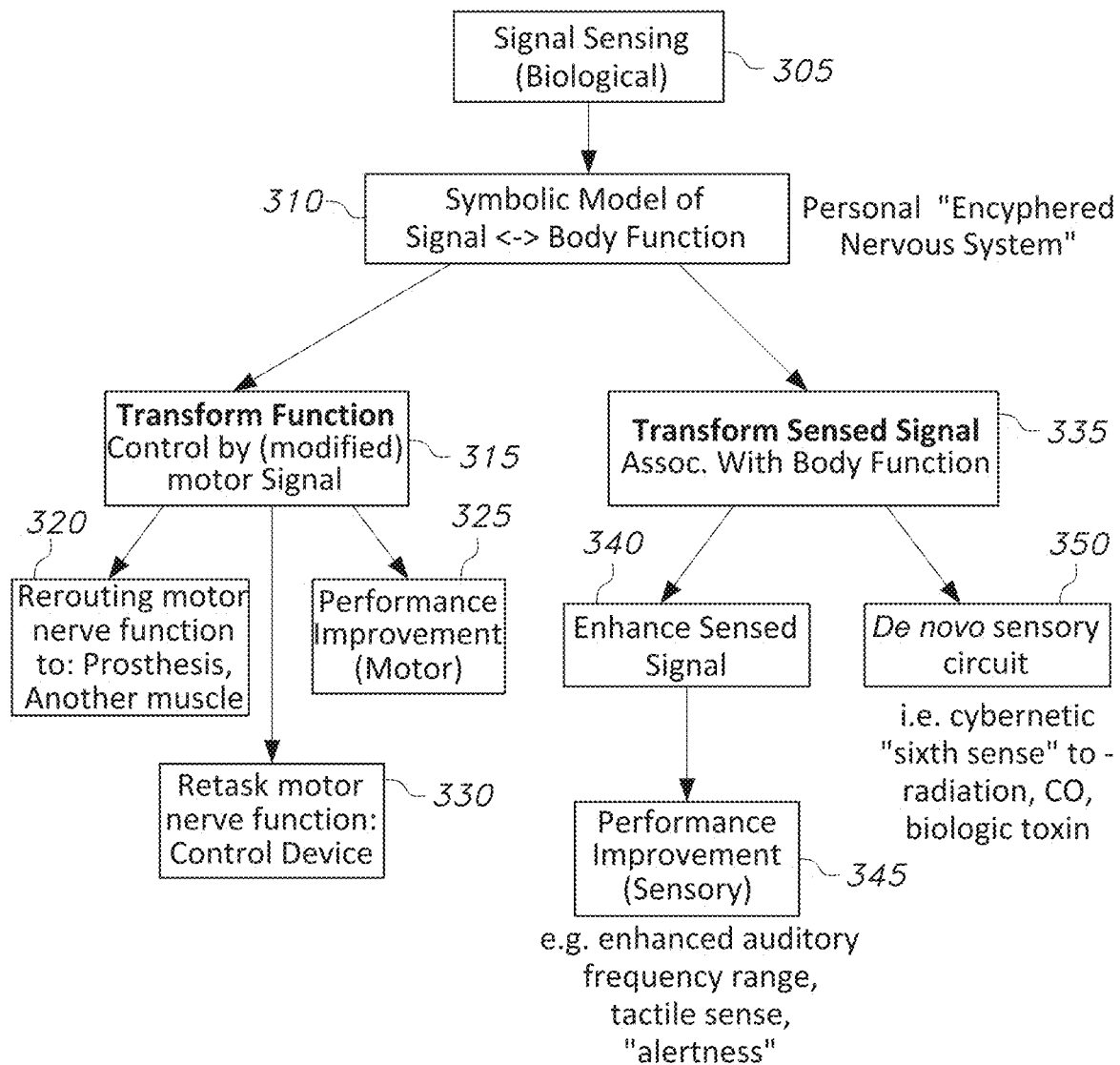
FIG. 3 is a flowchart indicating functionality of the invention for biological sensed signals.

FIG. 3 provides a flowchart for the ENS to sense biological signals (305) and complete an effector function based upon this information. The first step is the symbolic model, as described above (310). This involves mapping a sensed signal to a function—but not in the classical, detailed fashion typical of neurophysiology. This is a practical mapping step, for which mapping of secondary regions associated with a function is sufficient if that secondary region is readily accessible.

In FIG. 3, step 315 is to transform a function, controlled by an existing motor nerve (sensed biological signal). In step 320, the sensed signal is "re-routed" to control a prosthetic device or another muscle group. For instance, in the case of an amputee, the signature of motor nerve input to the leg may be detected from the skin above the amputation site. The range of sensed nerve activity on the skin may typically be 7-15 Hz (depending on the precise nerve). Sensing these signals, and mapping them to specific movement of a prosthetic limb may enable control of said limb. This control may require subsequent training—for instance, behavioral training in which the individual attempts to flex the amputated limb, and detecting the skin signals as those that will flex the prosthetic limb in that person. Similar personalized mapping is used to train other motions of the prosthesis. Thus, this invention represents one embodiment of a personalized "enciphered nervous system".

In FIG. 3, step 325 is a distinct function—to improve motor performance. It is well known that electrical stimulation of nerves that control a muscle can stimulate that muscle. The frequency and amplitude of this nerve activity lies within a range, but may be specific for an individual. Thus, this ENS function is to sense motor nerve activity controlling the quadriceps femoris muscle, for instance. The frequency and amplitude of nerve activity in regions of the skin associated with contraction and relaxation of that muscle are stored for an individual (part of the symbolic representation). An external device is then used to reiterate this functionality in a programmatic way. This can be used to stimulate the muscle during rest, to perform isometric exercises that will improve muscle function. This may also increase metabolic rate and cause weight loss.

In FIG. 3, step 330 is another distinct function—to retask biological motor activity to control a device. For instance, instead of actually moving a finger to control a remote control unit for an electronic device, the user may attempt to move that finger without expending sufficient energy to move the finger. Sensors on the finger are tuned detect this motor stimulation (that may be low amplitude), and the symbolic representation in the ENS converts this to signals representing play, pause, rewind or other functions and transmits them to control said consumer remote control unit. Clearly, this function can be extended to training an individual to move a portion of the face to represent the "play" function, and having a sensor transduce this function, and similarly for other surrogate regions of the body and retasked functions.

In FIG. 3, step 335 is a transformation of sensed signals. This is another functionality of the invention. Step 340 involves enhancing the sensed signal. An example is performance improvement (step 345), involving augmenting biological senses using sensors that detect outside of normally sensed ranges. For instance, sensing signals using a sensor of "inaudible to humans" part of the frequency spectrum, transducing the signal to the audible range, and transmitting it via vibration (bony conduction) to the hearing regions of the brain (auditory cortex) using a device could be used for private communication, encryption, recreational or other purposes. Medically, this invention could be used to compensate for hearing loss. This same invention with sensors of vibration could be used to compensate for loss of this sensation in certain neurological diseases such as peripheral neuropathy, by transmitting this sensation to an intact sensation in a different part of the body.

Another example of performance improvement (step 345) is to increase alertness. Stimulation of the scalp in the temporal region and other function-specific zones can increase brain activity in these regions. The invention tailors such stimulation to the symbolic representation of awakeness (i.e., alertness). As a corollary, drowsiness can be detected via the ENS and used as part of a feedback loop to trigger low intensity stimulation elsewhere on the body where a cutaneous device can be placed. This has several applications, including detecting and trying to prevent drowsiness while driving, in the intensive care unit during pre-comatose states or during drug-overdoses, and as a monitor for excessive alcohol or medication ingestion.

Sensors can detect alertness versus drowsiness from large groups of neurons such as using electroencephalography (EEG) that produce a wide range of frequencies. EEG signals, for instance, have a broad spectral content but exhibit specific oscillatory frequencies. The alpha activity band (8-13 Hz) can be detected from the occipital lobe (or, in this invention from electrodes placed over the occipital region of the scalp) during relaxed wakefulness and increase when the eyes close. The delta band is 1-4 Hz, theta from 4-8 Hz, beta from 13-30 Hz and gamma from 30-70 Hz. Faster EEG frequencies are linked to thought (cognitive processing) and alertness, and EEG signals slow during sleep and during drowsiness states such as coma and intoxication.

In FIG. 3, step 350 uses the invention for de novo sensory function. One example is creating a digital or cybernetic "sixth sense"—that is, adding to the existing 5 senses using external sensors to detect an extended set of stimuli. The set of sensors is nearly infinite, but includes several of particular relevance to the field of industrial or military use, including sensors for alpha or beta-radiation. Once sensed, the ENS transduces this signal to an existing sense, such as vibration delivered through a skin patch to a relatively unused skin region e.g., lower back. A combat soldier exposed to alpha or beta particles will now "feel" radiation as a programmable/trainable set of vibrations in his lower back. Similarly, sensors for carbon monoxide or other respiratory hazards could be transduced as "sixth senses" into—for instance—low frequency vibration on the nostril. This approach is far more efficient than a visual readout or other existing devices—because they use the ENS to essentially reprogram the natural nervous system for these functions.

Figure 4:
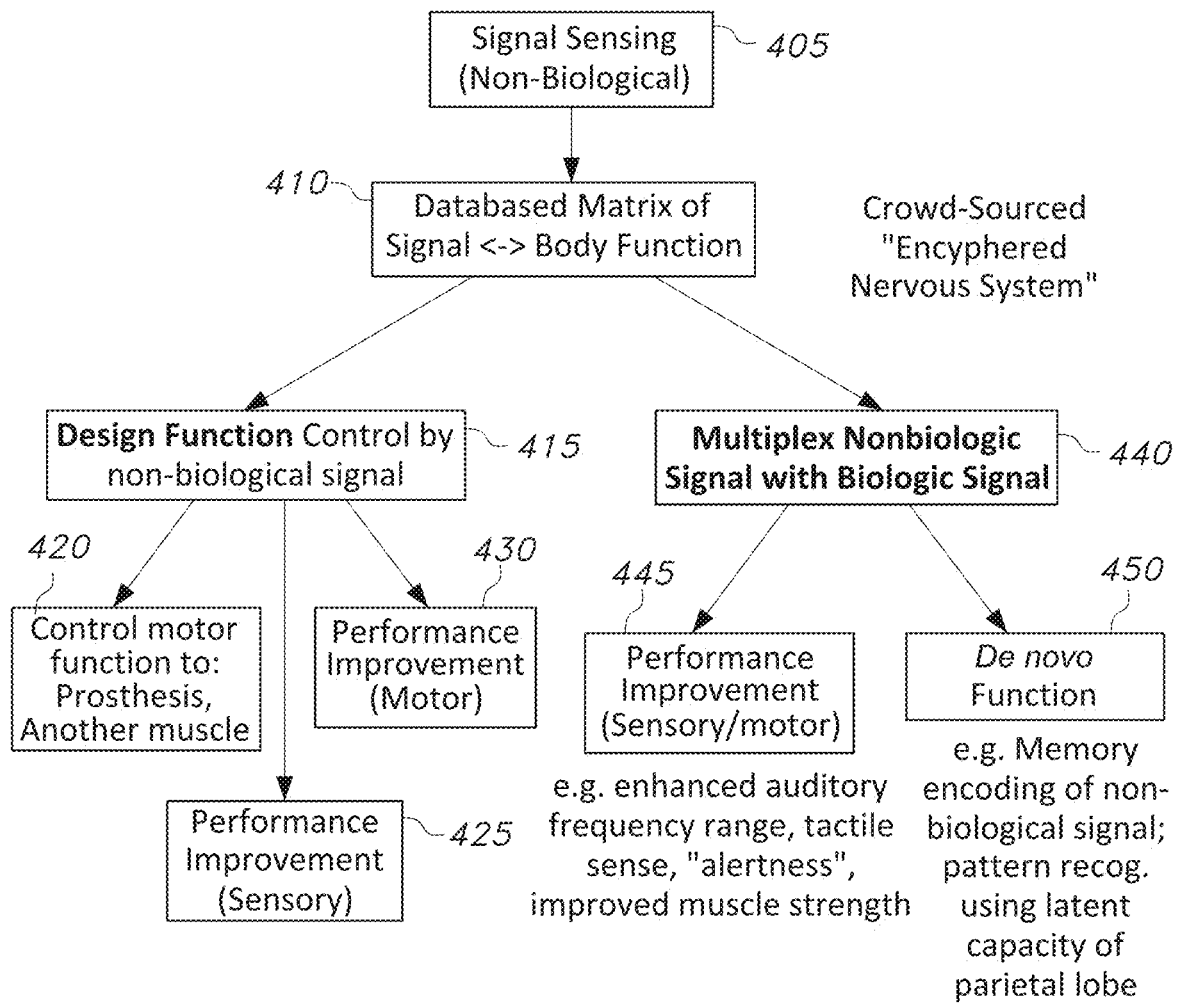
FIG. 4 is a flowchart indicating functionality of the invention for non-biological (external) sensed signals.

FIG. 4 illustrates a flowchart of an embodiment in which non-biological signals are sensed (step 405) and processed by the "enciphered nervous system". The symbolic representation between the body function and sensed signals is now extended to a non-personalized ENS (step 410), in order to incorporate external signals of a generic form albeit potentially tailored to the individual person. This ENS can be derived from a database of multiple individuals, or by a technique such as crowd-sourcing in which information from multiple persons connected by a social network is used to provide functionality.

Step 415 in FIG. 4 involves designing a programmable body function to be associated with the sensed external (non-biological) signal. This function can include motor control of a device such as prosthetic limb in step 420. Another example would be more far reaching—to use an external trigger signal to improve function in an existing natural muscle group (item 430). As described, skeletal muscle is typically stimulated by nerve activity at a frequency of 7-15 Hz (that varies with the precise nerve distribution, see Dorfman et al. Electroencephalography and Clinical Neurophysiology, 1989; 73: 215-224). Providing this stimulation can improve muscle strength by stimulating it, and would enable performance improvement of, e.g., leg muscles from a programmable signal. A medical example would be to treat central sleep apnea, by having an external sensor of oxygen desaturation to activate a device that stimulates the phrenic nerve and hence the diaphragm. This has substantial clinical implications.

In FIG. 4 step 425, the invention uses an external signal to improve performance in a sensory function. In an example already used, hearing can be enhanced by using external sensors of auditory signals outside the normal frequency range to be transduced to the normal frequency range as vibrations delivered via bone conduction to the cochlear nerve in the inner ear using a device placed near the mastoid processes (e.g., attached to the side-arms of eyeglasses).

In FIG. 4 step 440 the invention exploits the full potential of the enciphered nervous system to create novel programmable functionality by pairing an external sensed signal with intrinsic nervous function. The example of performance improvement (sensory or motor) in step 445 has been discussed.

In step 450, FIG. 4, the invention can provide de novo functionality. A large proportion of cerebral processing power is dormant at any given time, but may be activated subconsciously during daily activity (e.g., daydreaming) The ENS can programmatically access this capacity to use the intrinsic nervous system as a computer. One task for which the human brain/nervous system is particularly adept is pattern recognition. Recognition of faces, spatial patterns and other complex datasets is performed by people far better than by most artificial computers. The selected example trains the individual to detect said pattern via repeated exposure to an image. The biological response to this image (symbolic representation) is detected by sensors on the temporal or frontal scalp. Again, this is empirical mapping—and it is sufficient to represent a secondarily activated region of the brain/scalp. Once this is accomplished, then detection of the pattern or a similar pattern will subconsciously trigger said response, that can be sensed and coded as a "1" or "0" to control a device (e.g., a pattern classifier computer) or cause a certain function—such as to trigger an alarm if this is a dangerous pattern/image.

Figure 5:
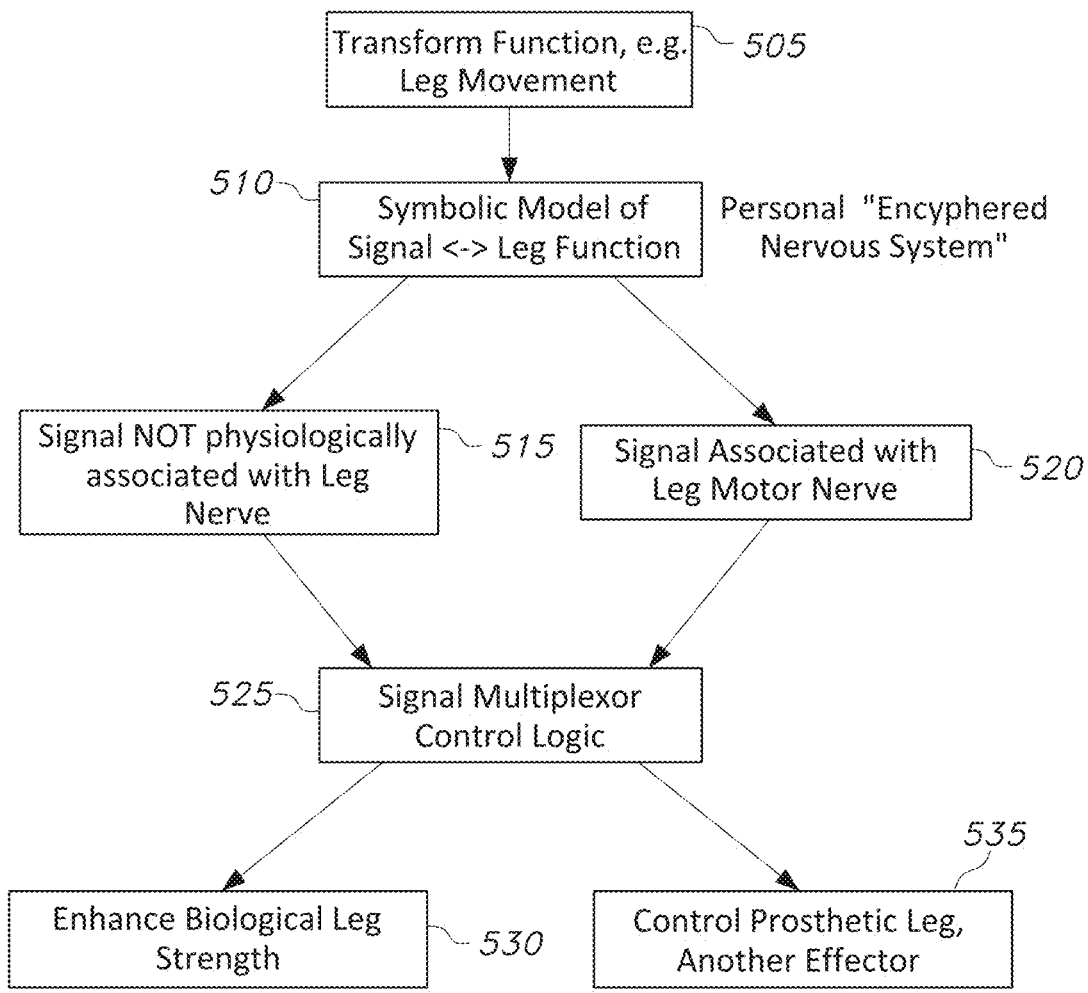
FIG. 5 is a flowchart indicating one embodiment for enhancing motor (muscle control) function of the nervous system. This is illustrated for leg muscle function, for enhancement (e.g., in military or sports use) or for medical purposes (e.g., after a stroke).

FIG. 5 provides a flowchart of a preferred embodiment to transform leg movement. A symbolic model of motor nerve function, sensed near the primary motor region (scalp, near the superior portion of the contralateral precentral gyrus) or at a secondary region, is associated with a plurality of leg motions in step 510. Once done, this functional mapping can be reprogrammed using external sensed signals (step 515) or signals not normally associated with leg function (e.g., moving an index finger in patients with leg disease or soldiers who cannot move their leg in a certain task), or the existing signal (step 520). In step 525 a signal multiplexor is able to mathematically associate the non-associated or associated signals in order to control the desired programmed function. In step 530 this is enhancement of the biological leg function (e.g., via cutaneous/direct electrical stimulation as described). In step 535 this is via control of a prosthetic limb.

Figure 6:
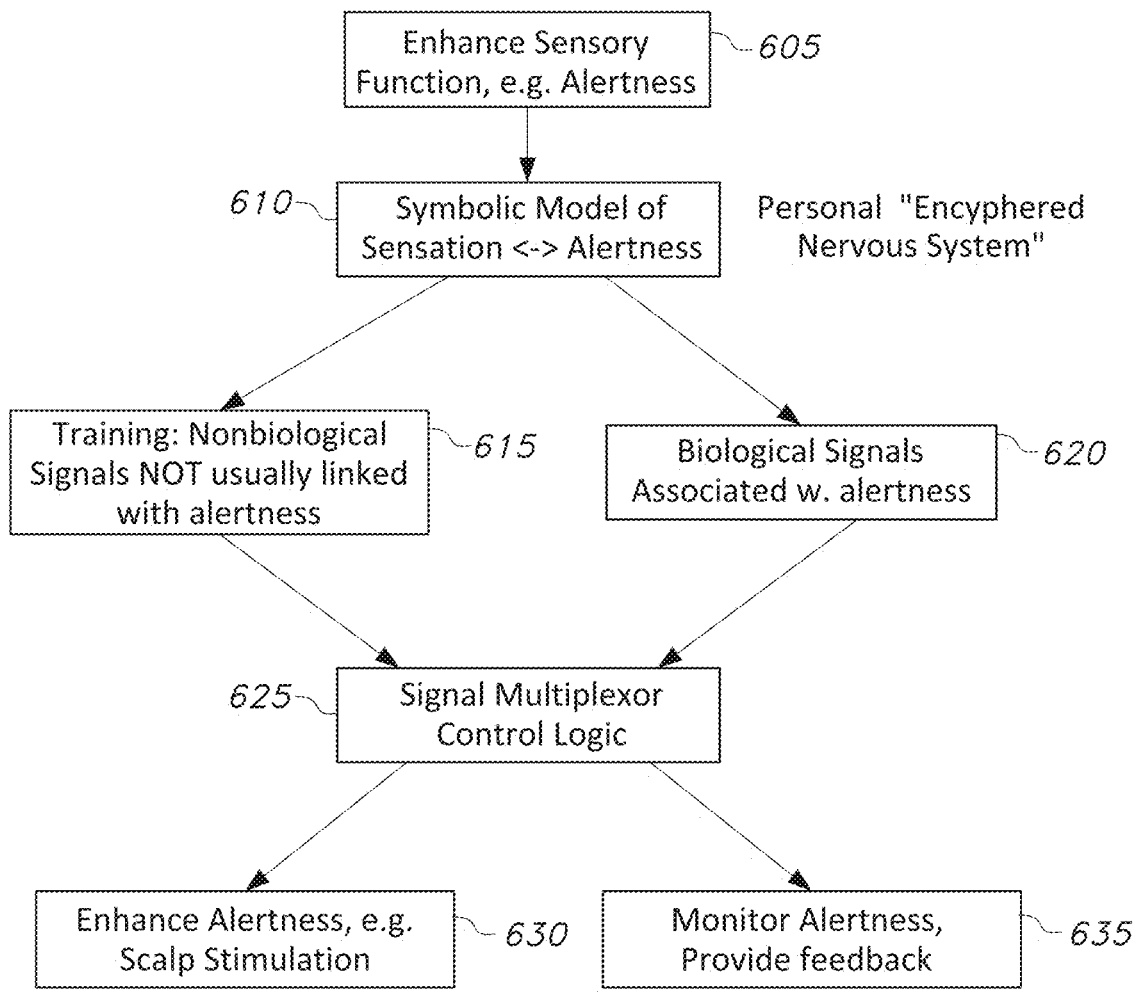
FIG. 6 is a flowchart indicating one embodiment for enhancing sensory perception/sensation of the nervous system. This is illustrated for alertness, for enhancement (e.g., military or sports use), for medical purposes (e.g., monitoring drowsiness or coma), or for consumer safety (e.g., identifying drowsiness while driving to control a feedback device).

FIG. 6 provides an embodiment for enhancing sensory alertness. The steps are analogous to the prior examples. The symbolic model of scalp sensed nerve activity, e.g., in the temporal region, is empirically associated with varying alertness levels (self-reported or monitored) in step 610. This functional mapping is reprogrammed using external sensed signals (step 615) or signals not normally associated with alertness (e.g., a specific auditory sensed frequency), or the existing scalp signal (step 620). In step 625 a signal multiplexor mathematically associates the non-associated or associated signals to program the desired function—electrical stimulation of the scalp to increase alertness (step 630). Step 635 provides an alertness monitor that can provide an alarm or actually result in stimulated function (to close the artificial/cybernetic feedback loop in the enciphered nervous system) to detect and try to avoid drowsiness, coma or toxin ingestion.

Figure 7:
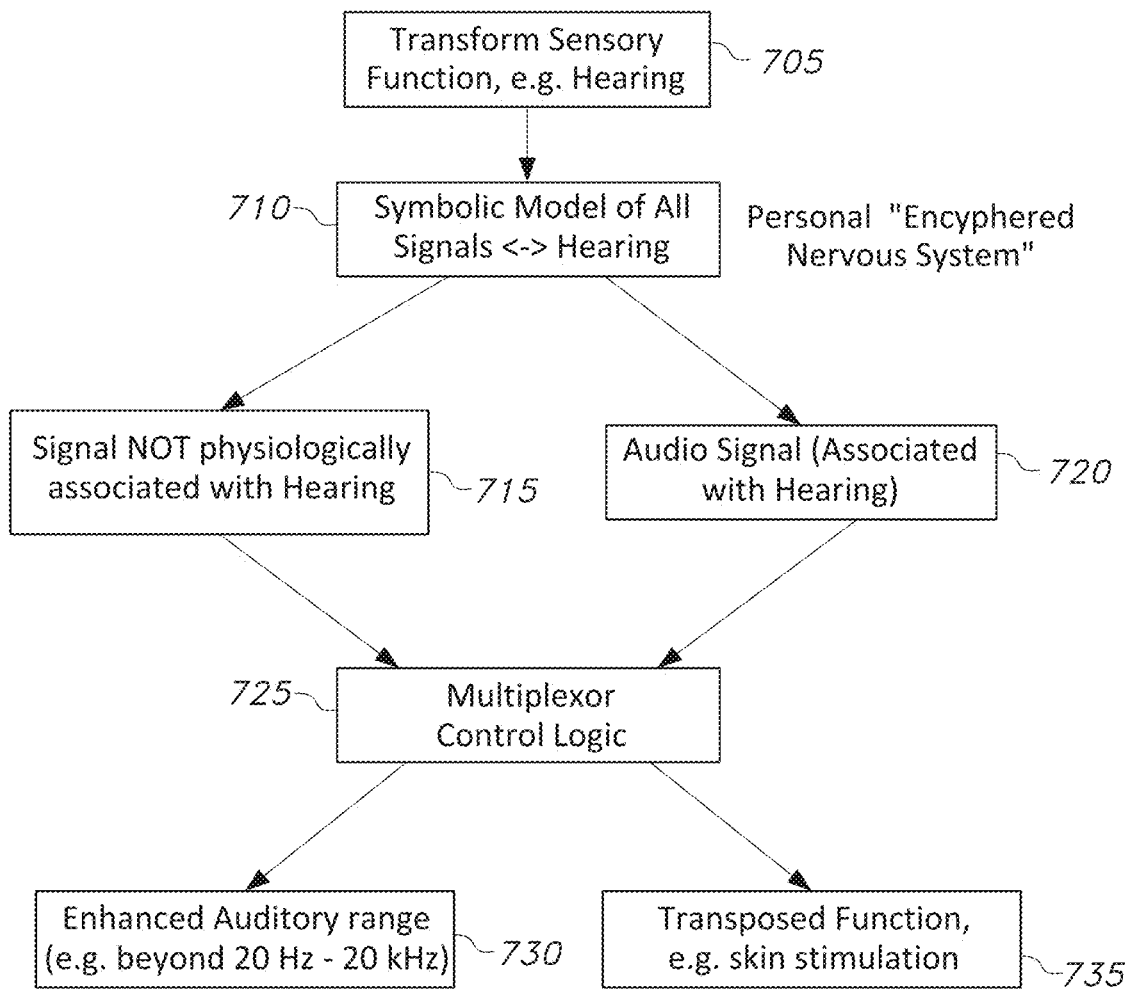
FIG. 7 is a flowchart indicating another embodiment for transposing or enhancing sensory perception. This is illustrated for hearing, with the invention enhancing hearing and transposing hearing function to another nervous function.

FIG. 7 is a flowchart of an embodiment to enhance performance in a sensory function—in this case hearing. Step 710 forms the symbolic representation using sensed signals from a readily accessible sensor (not just ear, but potentially secondarily associated skin regions). Step 715 uses sensors that detect outside of normally sensed ranges in "inaudible to humans" parts of the frequency spectrum. Step 720 uses a signal normally associated with hearing. Step 725 uses a multiplexor and control logic to transduce the signal to the audible range (step 730), transmitted via vibration (bony conduction) to the hearing regions of the brain (cochlear nerve/auditory cortex) using a device could be used for private communication, encryption, recreational or other purposes. Medically, this invention could be used to compensate for hearing loss. This same invention with sensors of vibration could be used to compensate for loss of this sensation in certain neurological diseases such as peripheral neuropathy, by transmitting this sensation to an intact sensation in a different part of the body. Step 735 transduces this signal to a different 'surrogate' sensation.

Figure 8:
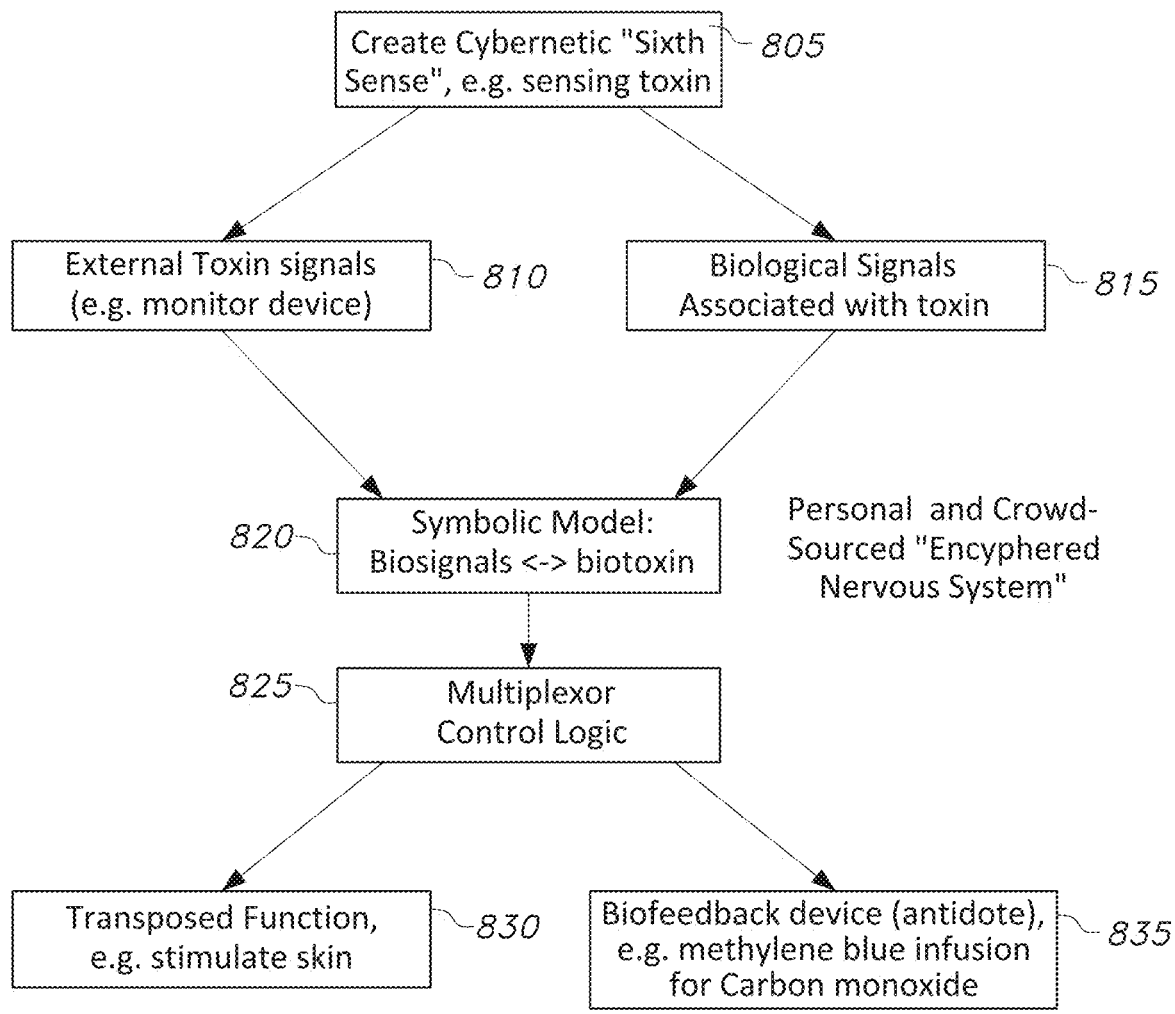
FIG. 8 is a flowchart indicating another embodiment for providing a sensory function that does not currently exist. This is illustrated for integrating sensation from a biosensor for a biotoxin.

FIG. 8 depicts an embodiment to use the ENS to integrate functionality that does not exist in nature into a personalized biofeedback loop—in this case, detecting a toxin. Examples include inhalation of Carbon monoxide, a toxic gas that is colorless, odorless, tasteless, and initially non-irritating, that is very difficult for people to detect. Another example is exposure to a biotoxin, that may not be sensed until symptoms and signs of a disease occur hours, days or weeks later. The inventive approach to provide a "sixth sense" (step 805) is cybernetic, since the toxin may produce both a direct signal from a specific sensor (detected at step 810) and an associated biological signal (step 815), that are blended (or multiplexed) in the invention. Examples of a direct signal from a dedicated sensor (element 810) are the chemical detection of carbon monoxide, or a biological assay for an infective agent (viruses, bacteria, fungi). Ideally, this sensor operates in near-real time, although this is not a requirement and if not the case will simply provide a slower, non-real time signal. Examples of an associated biological signal to carbon monoxide—a toxin that is traditionally considered 'unsensed'—is the specific cherry red colorimetric change of hemoglobin from carbon monoxide and the non-specific reduction in oxygenated hemoglobin that results when carbon monoxide binds to oxygen binding sites.

FIG. 8 further depicts that the enciphered nervous system of the invention forms an associative symbolic representation (step 820) between the direct and associated biological sensed signals. The symbolic relationship may include a direct mathematical transform, such as a quantitive relationship of the sensed signal to carbon monoxide or the associated biological signal of cherry red discoloration of hemoglobin to biologically relevant concentrations. The symbolic relationship may also use an artificial neural network or other pattern-learning or relational approaches to link, e.g., elevated heart rate or oxygen desaturation, to the toxin.

In FIG. 8 step 825, signals are multiplexed in a non-linear analytical fashion, as defined in the symbolic representation for any specific toxin. Computer logic is then used to control a biological or artificial effector device. Several therapy or monitor functions can be programmed to close a biofeedback loop. For instance, the signal from the normally unsensed toxin can be transduced into a specific signal on a naturally sensed 'channel' (step 830), e.g., low intensity vibration on skin on the nostril (intuitively linked with inhalation), or stimulation of skin over a scalp region normally associated with deoxygenation. This latter biofeedback uses information from training related to the individual person (contributing to the personalized enciphered nervous system), or a database of symbolic representations from many individuals associating related stimuli (here, de-oxygenation) to biological signals. This is an example of a population-based, or potentially crowd-sourced enciphered nervous system. Another biofeedback option is therapeutic (step 835)—delivery of an antidote, by sending control signals to a device. For carbon monoxide exposure, therapy includes increasing oxygen concentrations (using hyperbaric oxygen in extreme cases) and administering methylene blue.

Nomograms of the detrimental impact of sensed signals are used to calibrate sensing and delivery of therapy functions from the enciphered nervous system. For carbon monoxide, exposures at 100 ppm (0.01%) or greater can be dangerous to human health. Accordingly, in the United States, Federal agencies such as OSHA put a highest limit on long-term workplace exposure levels of 50 ppm, but individuals should not be exposed to an upper limit ("ceiling") of 100 ppm. Exposures of 800 ppm (0.08%) lead to dizziness, nausea, and convulsions within 45 min, with the individual becoming insensible within 2 hours. Clearly, detecting this toxin early would have extremely practical implications in industrial environments, for instance. Other nomograms can be developed to identify thresholds for "safe" versus and "actionable" exposure to various stimuli including but not limited to chemicals, biological toxins, radiation, electrical stimuli, visual stimuli and auditory stimuli.

Figure 9:
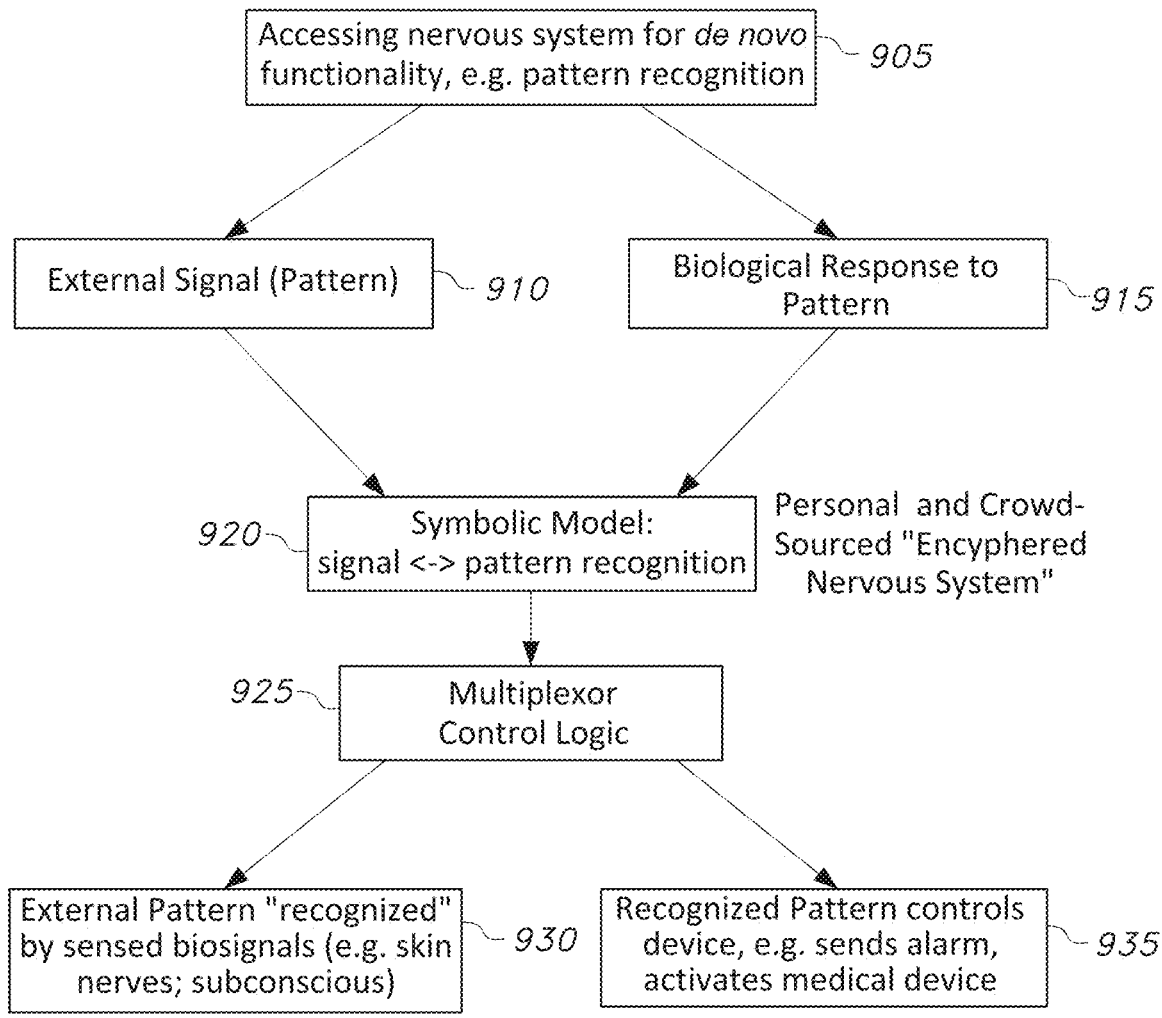
FIG. 9 is a flowchart indicating another embodiment for using the invention and enciphered nervous system to provide de novo functionality. Illustrated is using unused computational capacity of the nervous system to perform pattern recognition in lieu of programming an artificial computer for this purpose.

FIG. 9 provides a flowchart for an embodiment in which the enciphered nervous system enables access to the processing power of the natural nervous system to perform an arbitrary task, in this case pattern recognition (step 905). This embodiment of the invention is based upon 3 concepts. First, that the brain is more efficient at some tasks than even the most powerful and well-programmed artificial electronic computers. Pattern recognition, e.g., of faces, is an excellent example that is easily accomplished by most people yet that is suboptimal by computers even with very sophisticated programming. Second, that the brain output from a presented stimulation can be sensed. Third, that the brain has unused capacity that can be accessed for this purpose. This third item presents safety limits, and in the case of pattern recognition, the invention must not be used for bioencoding images or data that would be emotionally harmful or sensitive.

Steps 910 and 915 mathematically link the pattern (e.g., a face) to the biological sensed response—for instance, activity of nerves in the scalp over the parietal lobes of the brain, or over the forehead indicating "recognition". This is used to create the elements of enciphered nervous system for this task (step 920). This will be personalized, but can also take inputs from a multi-person (population, crowd-sourced) enciphered nervous system. Once this link has been made, then presentation of the pattern will result in a "sensed" biological pattern, that is used in step 925 to deliver a "1" (recognized) or "0" (not recognized) to control a device (step 930) (e.g., external computer classifier) or stimulate the individual via a surrogate sensation (step 935) (e.g., vibration at the left upper arm if a recognized pattern is detected). Uses for this invention include pure biocomputing (pattern recognition of familiar or abstract shapes/codes), formally encoding and enhancing memory of faces for a particular person, and security such that only a hostile pattern/face elicits a specific surrogate sensation or activates a device. One other advantage of this approach over waiting for a cognitive recognition of the pattern is that this can function as a "background process" and/or provide faster pattern recognition.

Figure 10:
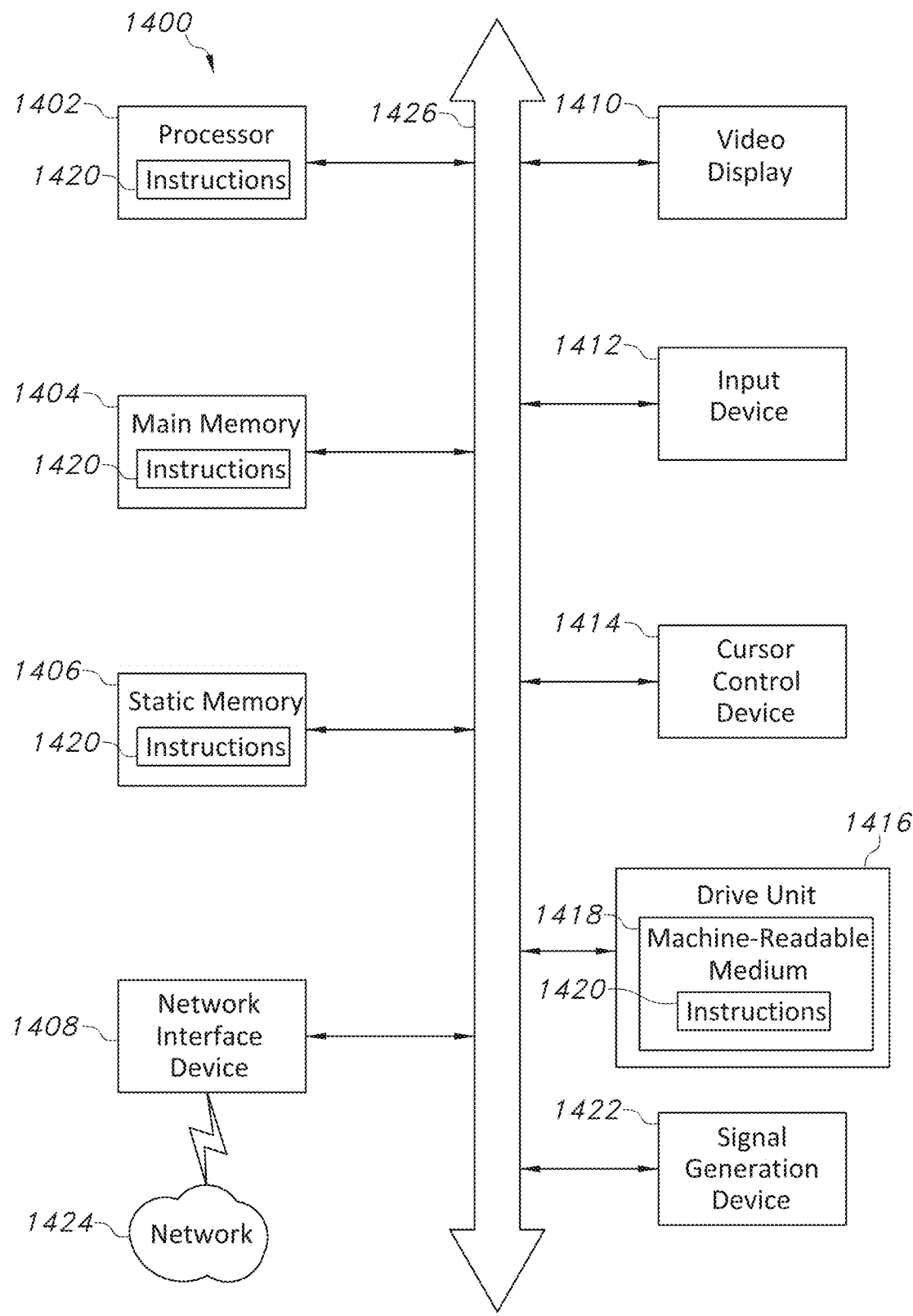
FIG. 10 is a block diagram of an illustrative embodiment of a general computer system.

FIG. 10 is a block diagram of an illustrative embodiment of a general computer system 1400. The computer system 1400 can be the signal processing device 114 and the computing device 116 of FIG. 1. The computer system 1400 can include a set of instructions that can be executed to cause the computer system 1400 to perform any one or more of the methods or computer based functions disclosed herein. The computer system 1400, or any portion thereof, may operate as a standalone device or may be connected, e.g., using a network or other connection, to other computer systems or peripheral devices. For example, the computer system 1400 may be operatively connected to signal processing device 114 and analysis database 118.

In operation as described in FIGS. 1-9, the modification or enhancement of the nervous system of the body by creating and using an enciphered nervous system (ENS) as described herein can be used to enhance performance in normal individuals or restore or treat lost function in patients.

The computer system 1400 may also be implemented as or incorporated into various devices, such as a personal computer (PC), a tablet PC, a personal digital assistant (PDA), a mobile device, a palmtop computer, a laptop computer, a desktop computer, a communications device, a control system, a web appliance, or any other machine capable of executing a set of instructions (sequentially or otherwise) that specify actions to be taken by that machine. Further, while a single computer system 1400 is illustrated, the term "system" shall also be taken to include any collection of systems or sub-systems that individually or jointly execute a set, or multiple sets, of instructions to perform one or more computer functions.

As illustrated in FIG. 10, the computer system 1400 may include a processor 1402, e.g., a central processing unit (CPU), a graphics-processing unit (GPU), or both. Moreover, the computer system 1400 may include a main memory 1404 and a static memory 1406 that can communicate with each other via a bus 1426. As shown, the computer system 1400 may further include a video display unit 1410, such as a liquid crystal display (LCD), an organic light emitting diode (OLED), a flat panel display, a solid state display, or a cathode ray tube (CRT). Additionally, the computer system 1400 may include an input device 1412, such as a keyboard, and a cursor control device 1414, such as a mouse. The computer system 1400 can also include a disk drive unit 1416, a signal generation device 1422, such as a speaker or remote control, and a network interface device 1408.

The invention may include, as depicted in FIG. 10, the disk drive unit 1416 may include a computer-readable medium 1418 in which one or more sets of instructions 1420, e.g., software, can be embedded. Further, the instructions 1420 may embody one or more of the methods or logic as described herein. In a particular embodiment, the instructions 1420 may reside completely, or at least partially, within the main memory 1404, the static memory 1406, and/or within the processor 1402 during execution by the computer system 1400. The main memory 1404 and the processor 1402 also may include computer-readable media.

The invention may also include, dedicated hardware implementations, such as application specific integrated circuits, programmable logic arrays and other hardware devices, can be constructed to implement one or more of the methods described herein. Applications that may include the apparatus and systems of various embodiments can broadly include a variety of electronic and computer systems. One or more embodiments described herein may implement functions using two or more specific interconnected hardware modules or devices with related control and data signals that can be communicated between and through the modules, or as portions of an application-specific integrated circuit. Accordingly, the inventive system encompasses software, firmware, and hardware implementations.

In accordance with the invention, the methods described herein may be implemented by software programs tangibly embodied in a processor-readable medium and may be executed by a processor. Further, in an exemplary, non-limited embodiment, implementations can include distributed processing, component/object distributed processing, and parallel processing. Alternatively, virtual computer system processing can be constructed to implement one or more of the methods or functionality as described herein.

It is also contemplated that a computer-readable medium includes instructions 820 or receives and executes instructions 1420 responsive to a propagated signal, so that a device connected to a network 1424 can communicate voice, video or data over the network 1424. Further, the instructions 1420 may be transmitted or received over the network 1424 via the network interface device 1408.

While the computer-readable medium is shown to be a single medium, the term "computer-readable medium" includes a single medium or multiple media, such as a centralized or distributed database, and/or associated caches and servers that store one or more sets of instructions. The term "computer-readable medium" shall also include any medium that is capable of storing, encoding or carrying a set of instructions for execution by a processor or that cause a computer system to perform any one or more of the methods or operations disclosed herein.

In a particular non-limiting, example embodiment, the computer-readable medium can include a solid-state memory, such as a memory card or other package, which houses one or more non-volatile read-only memories. Further, the computer-readable medium can be a random access memory or other volatile re-writable memory. Additionally, the computer-readable medium can include a magneto-optical or optical medium, such as a disk or tapes or other storage device to capture carrier wave signals, such as a signal communicated over a transmission medium. A digital file attachment to an e-mail or other self-contained information archive or set of archives may be considered a distribution medium that is equivalent to a tangible storage medium. Accordingly, any one or more of a computer-readable medium or a distribution medium and other equivalents and successor media, in which data or instructions may be stored, are included herein.

In accordance with the inventive embodiments, the methods described herein may be implemented as one or more software programs running on a computer processor. Dedicated hardware implementations including, but not limited to, application specific integrated circuits, programmable logic arrays, and other hardware devices can likewise be constructed to implement the methods described herein. Furthermore, alternative software implementations including, but not limited to, distributed processing or component/object distributed processing, parallel processing, or virtual machine processing can also be constructed to implement the methods described herein.

It should also be noted that software that implements the disclosed methods may optionally be stored on a tangible storage medium, such as: a magnetic medium, such as a disk or tape; a magneto-optical or optical medium, such as a disk; or a solid state medium, such as a memory card or other package that houses one or more read-only (non-volatile) memories, random access memories, or other re-writable (volatile) memories. The software may also utilize a signal containing computer instructions. A digital file attachment to e-mail or other self-contained information archive or set of archives is considered a distribution medium equivalent to a tangible storage medium. Accordingly, a tangible storage medium or distribution medium as listed herein, and other equivalents and successor media, in which the software implementations herein may be stored, are included herein.

Although specific example embodiments have been described, it will be evident that various modifications and changes may be made to these embodiments without departing from the broader scope of the invention. Accordingly, the specification and drawings are to be regarded in an illustrative rather than a restrictive sense. The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of any of the above-described embodiments, and other embodiments not specifically described herein, may be used and are fully contemplated herein.

The Abstract is provided to comply with 37 CFR § 1.72(b) and will allow the reader to quickly ascertain the nature and gist of the technical disclosure. It is submitted with the understanding that it will not be used to interpret or limit the scope or meaning of the claims.

In the foregoing description of the embodiments, various features are grouped together in a single embodiment for the purpose of streamlining the disclosure. This method of disclosure is not to be interpreted as reflecting that the claimed embodiments have more features than are expressly recited in each claim. Rather, as the following claims reflect, inventive subject matter lies in less than all features of a single disclosed embodiment. Thus the following claims are hereby incorporated into the Description of the Embodiments, with each claim standing on its own as a separate example embodiment.

What is claimed is:

1. A method of treating a sleep disorder, the method comprising:
   detecting signals associated with a plurality of symptoms or signs of the sleep disorder at a sensor disposed in relation to a human body;
   processing the signals to create a symbolic representation of the sleep disorder, wherein the symbolic representation indicates a relationship of the signals to the sleep disorder empirically and not based on physiologic mapping of the signals to the sleep disorder;
   stimulating a region of the human body to alter the symbolic representation between detected signals and the sleep disorder, wherein the symbolic representation as altered indicates treatment of the sleep disorder.

2. The method of claim 1, wherein the signals are detected on an extremity of the human body.

3. The method of claim 1, wherein the method further comprises directly transforming the symbolic representation from patterns of nerve firing during the stimulating.

4. The method of claim 1, wherein the symbolic representation is not directly transformed from patterns of nerve firing during the stimulating.

5. The method of claim 1, wherein the stimulating involves delivering energy to the scalp overlying brain regions associated with the sleep disorder.

6. The method of claim 1, wherein the stimulating involves delivering energy to regions of the human body associated with the sleep disorder not including the brain.

7. The method of claim 1, wherein the plurality of symptoms or signs includes a rate of breathing.

8. The method of claim 1, wherein the signals are associated with one or more of ventilating (breathing) rate, muscle movement, gastrointestinal function, body temperature, and electrical signals from the nervous system.

9. The method of claim 1, wherein the stimulating comprises delivering electrical stimuli, visual stimuli, and auditory stimuli.

10. The method of claim 9, wherein the visual stimuli include displays on a computer device selected from the group consisting a personal computer, a personal digital assistant, a mobile device, a palmtop computer, a laptop computer, a desktop computer, a communications device, a control system, a web appliance, and one or more combinations thereof.

11. The method of claim 9, wherein the auditory stimuli include sounds from a computer device selected from the group consisting of a personal computer, a personal digital assistant, a mobile device, a palmtop computer, a laptop computer, a desktop computer, a communications device, a control system, a web appliance, and one or more combinations thereof.

12. The method of claim 1, wherein the sleep disorder is a sleep apnea.

13. The method of claim 12, wherein the sleep apnea is a central sleep apnea or obstructive sleep apnea.

14. A system to treat a sleep disorder, the system comprising:
   a processor;
   a memory storing instructions that, when executed by the processor, perform operations comprising:
      detecting signals associated with a plurality of symptoms or signs of the sleep disorder at a sensor disposed in relation to a human body;
      processing the signals to create a symbolic representation of the sleep disorder, wherein the symbolic representation indicates a relationship of the signals to the sleep disorder empirically and not based on physiologic mapping of the signals to the sleep disorder;
      stimulating a region of the human body to alter the symbolic representation between detected signals and the sleep disorder, wherein the symbolic representation as altered indicates treatment of the sleep disorder.

15. The system of claim 14, wherein the signals are detected on an extremity of the human body.

16. The system of claim 14, wherein the operations further comprise directly transforming the representation from patterns of nerve firing during the stimulating.

17. The system of claim 14, wherein the symbolic representation is not directly transformed from patterns of nerve firing during the stimulating.

18. The system of claim 14, wherein the operation of stimulating comprises delivering electrical impulses to the scalp overlying brain regions associated with the sleep disorder.

19. The system of claim 14, wherein the operation of stimulating comprises delivering energy to regions of the body associated with the sleep disorder not including the brain.

20. The system of claim 14, wherein the plurality of symptoms or signs includes a rate of breathing.

21. The system of claim 14, wherein the signals are associated with one or more of ventilating (breathing) rate, muscle movement, gastrointestinal function, body temperature, and electrical signals from the nervous system.

22. The system of claim 14, wherein the operation of stimulating comprises delivering electrical stimuli, visual stimuli, and auditory stimuli.

23. The system of claim 22, wherein the visual stimuli include displays on a computer device selected from the group consisting a personal computer, a personal digital assistant, a mobile device, a palmtop computer, a laptop computer, a desktop computer, a communications device, a control system, a web appliance, and combinations thereof.

24. The system of claim 22, wherein the auditory stimuli include sounds from a computer device selected from the group consisting of a personal computer, a personal digital assistant, a mobile device, a palmtop computer, a laptop computer, a desktop computer, a communications device, a control system, a web appliance, and combinations thereof.

25. The system of claim 14, wherein the sleep disorder is a sleep apnea.

26. The system of claim 25, wherein the sleep apnea is a central sleep apnea or obstructive sleep apnea.

* * * * *